(12) United States Patent
Figg et al.

(10) Patent No.: US 11,279,910 B2
(45) Date of Patent: Mar. 22, 2022

(54) DISPENSING METHOD AND APPARATUS

(71) Applicant: Solentim Ltd, Wimborne (GB)

(72) Inventors: Aaron Figg, Wimborne (GB);
Yonggang Jiang, Wimborne (GB)

(73) Assignee: Solentim Ltd

( * ) Notice: Subject to any disclaimer, the term of this patent is extended or adjusted under 35 U.S.C. 154(b) by 581 days.

(21) Appl. No.: 15/603,184

(22) Filed: May 23, 2017

(65) Prior Publication Data

US 2017/0342367 A1    Nov. 30, 2017

(30) Foreign Application Priority Data

May 31, 2016  (GB) ..................................... 1609508

(51) Int. Cl.
| | | |
|---|---|---|
| *C12M 1/36* | (2006.01) | |
| *C12M 1/00* | (2006.01) | |
| *G06K 9/00* | (2006.01) | |
| *G06T 7/70* | (2017.01) | |
| *C12M 1/34* | (2006.01) | |
| *C12Q 3/00* | (2006.01) | |
| *H04N 5/225* | (2006.01) | |

(52) U.S. Cl.
CPC ............ *C12M 41/48* (2013.01); *C12M 41/36* (2013.01); *C12M 47/04* (2013.01); *C12Q 3/00* (2013.01); *G06K 9/00127* (2013.01); *G06T 7/70* (2017.01); *H04N 5/2257* (2013.01); *G06T 2207/30242* (2013.01)

(58) Field of Classification Search
CPC ............ G06T 7/70; G06T 2207/30242; C12M 41/36; C12M 41/48; C12M 47/04; G06K 9/00127; H04N 5/2257; C12Q 3/00
See application file for complete search history.

(56) References Cited

U.S. PATENT DOCUMENTS

| | | | |
|---|---|---|---|
| 8,086,016 B2 * | 12/2011 | Kobayashi et al. ........................ | |
| | | | G01N 21/6458 |
| | | | 382/128 |
| 2007/0148763 A1 | 6/2007 | Huh et al. | |
| 2009/0203063 A1 | 8/2009 | Wheeler et al. | |
| 2015/0064768 A1 * | 3/2015 | Kapre ..................... | C12N 7/00 |
| | | | 435/238 |

(Continued)

FOREIGN PATENT DOCUMENTS

| | | |
|---|---|---|
| EP | 1950282 A1 | 7/2008 |
| GB | 2316081 A | 2/1998 |

(Continued)

OTHER PUBLICATIONS

Combined Search and Examination Report issued in Great Britain Patent Application No. 1609508.5, dated Mar. 7, 2017 (9 pages).

*Primary Examiner* — Gautam Prakash
(74) *Attorney, Agent, or Firm* — Ferguson Braswell Fraser Kubasta PC (57) ABSTRACT

There is provided an apparatus comprising a receptacle to receive a sample. A sample dispenser dispenses the sample into the receptacle and an image capture device captures an image of the sample in the receptacle. Processing circuitry processes the image to determine whether the receptacle contains zero cells, exactly one cell, or more than one cell. In response to the processor determining that the receptacle contains zero cells, the processing circuitry causes the sample dispenser to dispense a further sample into the receptacle.

16 Claims, 5 Drawing Sheets

(56) References Cited

U.S. PATENT DOCUMENTS

2015/0192511 A1 7/2015 Wagner et al.
2016/0245813 A1* 8/2016 Mir et al. .............. B01L 3/5085

FOREIGN PATENT DOCUMENTS

WO 2007120240 A2 10/2007
WO 2012072822 A1 6/2012

* cited by examiner

DISPENSING METHOD AND APPARATUS

CROSS-REFERENCE TO RELATED APPLICATIONS

This application claims priority under 35 U.S.C. § 119(a) to GB Application No. 1609508.5, which filed on May 31, 2016. Accordingly, GB Application No. 1609508.5 is hereby incorporated by reference in its entirety.

The present technique relates to a particle dispensing method and apparatus. For example, the present technique may have relevance to the field of cell dispensing.

BACKGROUND

It is often desirable to be capable of dispensing exactly one particle (such as a cell) from a container of particles into a receptacle (such as a well of a microtiter well plate). For example, medical research such as for drug approval might call for the cultivation of a single cell. This process usually involves providing a reservoir containing a growth medium in which a concentration of cells are provided, and using a pump together with a dispensing tube whose width is very slightly larger than a single cell, to take a sample from the reservoir and place it in to its own receptacle. The size of each sample and the concentration of the cells in the growth medium in the reservoir are chosen so that, with some degree of probability, a sample will contain a single cell. Each sample is then cultivated over a period of time (e.g. 72 hours). In this way, a number of cultivations take place and the results can be averaged. However, this process suffers from a number of drawbacks. Firstly, there is no guarantee that any given sample will contain a cell. Such cultivation attempts therefore fail. If the number of successful cultivations is too low, the entire process may be considered a failure and may have to begin again. Secondly, any given sample might contain more than one cell. This is especially true if the concentration is increased in order to inhibit samples from containing zero cells. However, in this case, the cultivation results might be incorrect, since they refer to the cultivation of multiple cells rather than the cultivation of a single cell. Worse still, it may not be possible to determine that multiple cells were dispensed in the first place. It would therefore be desirable to improve the chances of performing cultivation on a single cell.

BRIEF SUMMARY

Viewed from a first example configuration, there is provided an apparatus comprising: a receptacle to receive a sample; a sample dispenser to dispense the sample into the receptacle; an image capture device to capture an image of the sample in the receptacle; and processing circuitry to process the image to determine whether the receptacle contains zero cells, exactly one cell, or more than one cell, wherein in response to the processor determining that the receptacle contains zero cells, the processing circuitry causes the sample dispenser to dispense a further sample into the receptacle.

Viewed from a second example configuration, there is provided a method comprising: dispensing a sample into a receptacle; capturing an image of the sample in the receptacle; and processing the image to determine whether the receptacle contains zero cells, exactly one cell, or more than one cell, wherein in response to determining that the receptacle contains zero cells, a further sample is dispensed into the receptacle.

Viewed from a third example configuration, there is provided an apparatus comprising: means for dispensing a sample into a receptacle; means for capturing an image of the sample in the receptacle; and means for processing the image and for determining whether the receptacle contains zero cells, exactly one cell, or more than one cell, wherein in response to determining that the receptacle contains zero cells, the means for dispensing the sample into the receptacle dispenses a further sample into the receptacle.

BRIEF DESCRIPTION OF THE DRAWINGS

The present technique will be described further, by way of example only, with reference to embodiments thereof as illustrated in the accompanying drawings, in which.

DETAILED DESCRIPTION OF EMBODIMENTS

Before discussing the embodiments with reference to the accompanying figures, the following description of embodiments and associated advantages is provided.

In accordance with one example configuration there is provided an apparatus comprising: a receptacle to receive a sample; a sample dispenser to dispense the sample into the receptacle; an image capture device to capture an image of the sample in the receptacle; and processing circuitry to process the image to determine whether the receptacle contains zero cells, exactly one cell, or more than one cell, wherein in response to the processor determining that the receptacle contains zero cells, the processing circuitry causes the sample dispenser to dispense a further sample into the receptacle.

A sample, containing zero, one, or more than one cell is dispensed into a receptacle. By using an image capture device to capture an image of the sample when it is in the receptacle, and by subsequently processing the image, it is possible to determine whether the dispensed sample contains zero cells, one cell, or more than one cell. In this example configuration, if it is determined that there are zero cells, the process is repeated by the processing circuitry causing another sample to be dispensed. In this way, it is possible to reduce or even eliminate the situation in which the receptacle contains zero cells. This is achieved without requiring an increased concentration of cells, which might increase the probability of a sample containing more than one cell, which is undesirable. Hence, it is more likely that cultivation can be attempted using a single cell as opposed to zero cells or more than one cell.

In some embodiments, the apparatus further comprises an actuator to move the sample dispenser relative to the receptacle, wherein in response to the processor determining that the receptacle contains zero cells, the actuator moves the receptacle relative to the sample dispenser to dispense a further sample into the receptacle. The movement performed by the actuator is very slight and continues to position the dispenser such that samples will be dispensed into the same receptacle. However, by performing such a slight movement, it is possible to reduce the chances of multiple samples being dispensed on top of each other. Accordingly, it is less likely that one cell will eclipse another and so it is more likely that the processing circuitry will correctly determine whether the receptacle contains zero cells, one cell, or more than one cell once the further samples has been dispensed into the receptacle. For example, the movement might be such that the dispenser's original location as adjusted by the movement would still cause the further sample to be dispensed into the same receptacle.

In some embodiments, in response to the processing circuitry determining that the receptacle contains more than one cell, the processing circuitry performs an error action. As previously explained, it is undesirable for a receptacle to contain more than one cell, since this can produce erroneous results. However, if it is known, ahead of time, that a receptacle contains more than one cell, then an error action can be taken in order to mitigate the effect of multiple cells in a single receptacle. In some examples, the error action comprises notifying a user that the receptacle comprises more than one cell. The user can therefore take appropriate action to either disregard that particular receptacle or perhaps clear the receptacle so that a further attempt at dispensing a sample having a single cell can be made. In other examples, the error action comprises storing data to indicate that the receptacle comprises more than one cell. Such information could be reported to the user at the end of the process. Alternatively, if further operations are performed on the receptacle, the stored information could be used as an internal reference to disregard results or not perform operations on the receptacle in question. It will be appreciated that the error action may comprise a number of sub-actions including those mentioned here, together with others that would occur to the skilled person.

In some embodiments, the apparatus further comprises a growth medium dispenser to dispense growth medium into the receptacle, wherein in response to the processing circuitry determining that the receptacle contains exactly one cell, the processing circuitry is to cause the growth medium dispenser is to dispense growth medium into the receptacle. The sample may comprise a small amount of growth medium in order to keep the cells active, but not a sufficient amount of growth medium to allow full cultivation to take place. Consequently, it is possible to dispense a large number of samples without the receptacle overflowing. In contrast, in embodiments where all the growth medium is provided together with the cell, there must be sufficient growth medium to encourage cultivation. However, if this is too large, then it may not be possible to dispense many (or even more than one) sample without the receptacle overflowing, which could ruin other nearby receptacles. Furthermore, by reducing the growth medium provided as part of the sample, and instead providing the growth medium after it has been established that exactly one cell is within the receptacle, it is possible to improve the processing performed by the processing circuitry. This is because there is less additional matter in the receptacle that might interfere with the detection of cells in the receptacle. Furthermore, it is less likely that a cell could be carried by the growth medium onto the walls of the receptacle, which again can make it difficult for the cell to be detected.

In some embodiments, the apparatus further comprises an actuator to move a plurality of receptacles, including the receptacle, relative to the sample dispenser; in response to the processing circuitry determining that the receptacle contains one or more cells, the processing circuitry is to cause relative movement between the sample dispenser and the plurality of receptacles so that the sample dispenser dispenses subsequent samples into a different receptacle in the plurality of receptacles. In this way, when it is determined that a receptacle contains zero cells, a further sample is dispensed into the receptacle. However, when it is determined that a receptacle contains one or more cells, the dispenser is moved so that future samples are dispensed into a different receptacle. Hence, a number of receptacles such as the wells in a microtiter well plate can be efficiently filled in such a manner that cultivation is more likely to occur using a single cell in each of the receptacles.

In some embodiments, in response to the processing circuitry determining that a first predefined proportion of dispensed samples each contain zero cells, the processing circuitry causes a user to be alerted. In such cases, if a predefined proportion of dispensed samples contain zero cells, then it is likely that the concentration of cells is inappropriate (e.g. too low). It can therefore be helpful to alert the user, who can thereby confirm whether or not the concentration is appropriate and correct the concentration if necessary. The predefined proportion could be based on an overall percentage (e.g. 85%), a fixed number (e.g. 5), a sliding window (6 out of the last 10), an average number of cells (0.7) dispensed per sample, or another statistical representation that will be known to the skilled person. Alternatively, or as well as alerting the user, the volume of each dispensed sample can be increased. As a consequence of increasing the volume of each dispensed sample, it is more likely that a given sample will contain a cell.

In some embodiments, a plurality of initially dispensed samples including the first predefined proportion of dispensed samples is dispensed into a subset of the plurality of receptacles, wherein the subset of the plurality of receptacles is less than the first predefined proportion of dispensed samples. Consequently, a small number of receptacles (e.g. one) is used in order to determine the concentration of the mixture and take action if the concentration is too low. In particular, the size of the subset is less than the first predefined proportion of dispensed samples such that fewer receptacles are used as compared to the number of samples that are dispensed, thereby reducing the number of receptacles required to determine if action need be taken.

In some embodiments, in response to the processing circuitry determining that a second predefined proportion of dispensed samples each contain more than one cell, the processing circuitry causes a user to be alerted. Another indicator that the concentration of cells is incorrect is if a (second) predefined proportion of dispensed samples each contain more than one cell. In this case, this would suggest that the concentration was too high. The second predefined proportion could be based on an overall percentage (e.g. 85%), a fixed number (e.g. 5), a sliding window (6 out of the last 10), an average number of cells (2.7) dispensed per sample, or another statistical representation that will be known to the skilled person. Alternatively, or as well as alerting the user, the volume of each dispensed sample can be decreased. As a consequence of decreasing the volume of each dispensed sample, it is less likely that a given sample will contain a cell.

In some embodiments, a plurality of initially dispensed samples including the second predefined proportion of dispensed samples is dispensed into a subset of the plurality of receptacles, wherein the subset of the plurality of receptacles is less than the second predefined proportion of dispensed samples. Consequently, a small number of receptacles (e.g. one) is used in order to determine the concentration of the mixture and take action if the concentration is too high. In particular, the size of the subset is less than the second predefined proportion of dispensed samples such that fewer receptacles are used as compared to the number of samples that are dispensed, thereby reducing the number of receptacles required to determine if action need be taken.

It will be appreciated that in the above embodiments, the same dispensed samples can be used to both determine if the first predefined proportion of dispensed samples each contain zero cells and/or if the second predefined proportion of dispensed samples each contain more than one cell. In other words, a number of samples could be dispensed into a subset of the receptacles (less than the number of samples) in order to determine whether the number of cells being dispensed is too high or too low, and thereby alert the user and/or adjust the volume of each dispensed sample to compensate.

In some embodiments, the apparatus further comprises output circuitry to output the image. Examples of such output circuitry could include a printer, a hard disk, or other form of storage. Accordingly, the image can be used to illustrate what the resulting cultivation started from. In the case where the image is of a single cell, this can be used as evidence that the resulting cultivation occurred from a single cell. Note that in some cases, the image can be stored as part of the error action that takes place if more than one cell is detected in the well.

In some embodiments, the apparatus further comprises a reservoir to hold a plurality of samples, connected to the sample dispenser; and an agitator to agitate the plurality of samples in the reservoir such that cells within the plurality of samples are distributed. The agitator could, for example, be an oscillator or simply a mixing apparatus to continually distribute cells in the reservoir. This can be used to prevent the cells from settling to the bottom of the reservoir and helps to maintain an equal distribution/dispersal of cells such that the probability of a sample containing a cell will be approximately in accordance with the concentration of cells in the reservoir.

Note that throughout this description, the term "cell" is used. However, the present technique relates equally to particles other than cells, which could be provided in a growth medium or other suspension.

Particular embodiments will now be described with reference to the figures.

Figure 1:
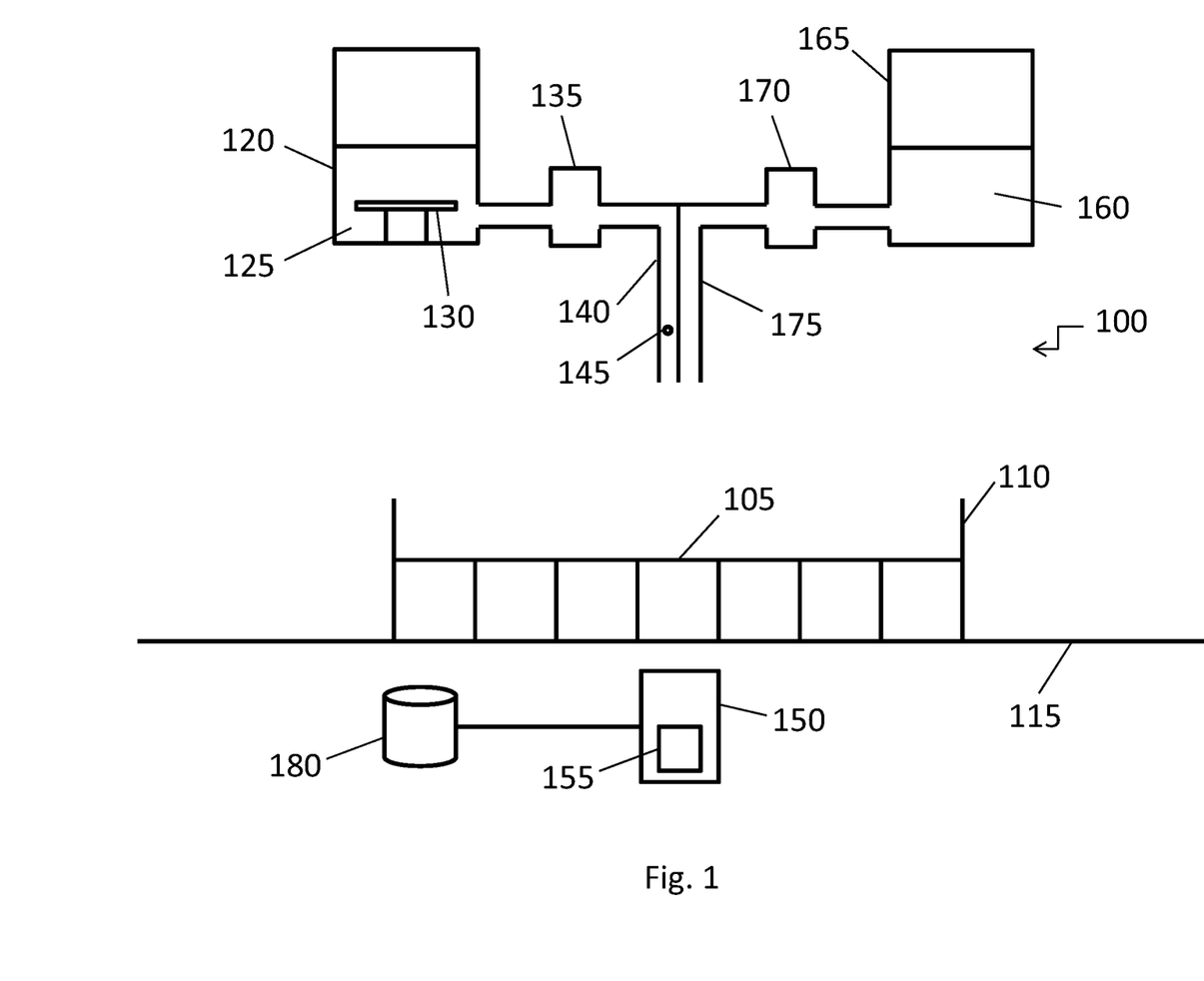
FIG. 1 illustrates an example apparatus in accordance with one embodiment.

FIG. 1 illustrates an example apparatus in accordance with one embodiment. The apparatus 100 includes a well 105 (an example of a receptacle), which forms part of a microtiter well plate 110 together with a plurality of other wells. The well 105 is able to move along a track 115 by virtue of the microtiter well plate moving along the track 115, the microtiter well plate being placed on a carriage connected to an actuator such as a screw turned by a motor controlled by a control system. A reservoir 120 contains a mixture 125 comprising a number of cells mixed together with a growth medium. An agitator 130 agitates the mixture 125 so as to evenly distribute the cells within the growth medium and discourage the cells from settling in the reservoir 120. A pump 135 is provided to extract a small quantity of the mixture 125 (a sample) from the reservoir and to dispense the sample through a tube 140 into a well 105. In this embodiment, the well 105 is located beneath the tube 140. The tube 140 is such that it is just wide enough to pass one of the cells. Accordingly, for a given concentration of cells in the mixture 125 and for a given sample size, there is a probability with which a sample will contain a single cell 145. In this example, the pump 135 and tube 140 collectively make up a dispenser. An image capture device 150 captures an image of the sample in the well 105 once the sample has been dispensed into the well 105. Processing circuitry 155 processes the image and determines, through image analysis, whether the sample or samples in the well 105 contain zero cells, one cell, or more than one cell. The action that is subsequently taken depends on which of these three conditions is met.

In the event that zero cells are detected, the well 105 and the tube 140 are moved relative to one another while still keeping a position such that a subsequent sample will be dispensed into the well 105. In other words, the well 105 and the tube 140 are moved relative to each other such that a subsequent sample will be dispensed into a different part of the well 105. In this example, the relative movement occurs by the microtiter well plate 110 being moved slightly along the track 115.

In the event that one cell is detected, growth medium 160 stored in a secondary reservoir 165 is provided by using a secondary pump 170 and a secondary dispensing tube 175. Sufficient growth medium is provided to the well 105 in order to encourage cultivation of cells whilst not over-filling the well 105. By providing the majority of the growth medium 160 after it has been established that the well 105 includes a single cell, it is possible to dispense numerous samples without the well 105 overfilling. Furthermore, due to the limited amount of growth medium in the well, it is less likely that a cell will be carried to one of the walls of the well 105, which would make accurate image analysis more difficult or even impossible. Once the growth medium 160 has been dispensed, the microtiter well plate 110 is moved so that a subsequent sample will be dispensed into an unused well, i.e. a well that has not had any samples dispensed into it during the process. Furthermore, the image of the sample in the well 105 is stored in a storage medium 180 for later retrieval by the user.

In the event that more than one cell is detected, an error action is performed. In this embodiment, the error action includes making note of the particular well 105 into which the sample was dispensed. For example a number or other identifier that uniquely identifies the well 105 in the microtiter well plate 110 is made. At the end of the overall process, the user is informed of those wells that were marked. In this embodiment, the image of the well 105 having more than one cell is stored in a storage medium 180 for later retrieval by the user.

In any of the above cases, unless the last well has been filled, the process is repeated, with another sample being dispensed.

As a consequence of the above, it is possible to reduce the number of occasions in which a well contains zero cells. Furthermore, since the majority of the growth medium is only added if and when a well contains a single cell, it is possible to add a large number of samples to an individual well without the well overflowing. Consequently, the concentration of the mixture can be lowered as compared to any similar systems since the scenario of a sample containing zero cells can be easily corrected for by dispensing further samples and the scenario of a sample containing more than one cell (which may not be easily corrected) will occur more rarely.

Figure 2:
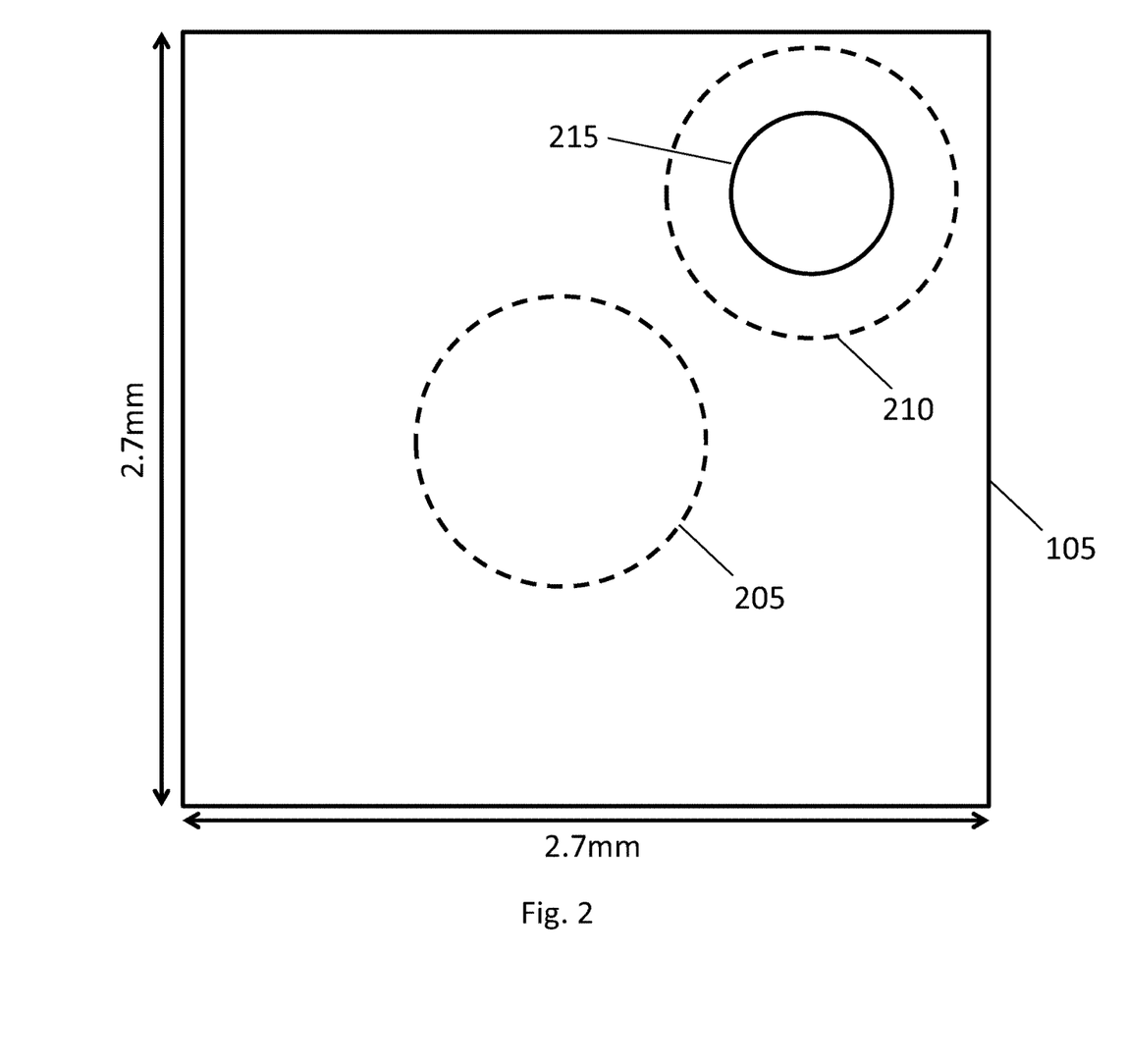
FIG. 2 shows a receptacle after dispensing a first sample having zero cells and a second sample having one cell.

FIG. 2 shows a receptacle, e.g. well 105 after dispensing a first sample 205 having zero cells and a second sample 210 having one cell 215. In this example, the well 105 has an area of 2.7 mm by 2.7 mm and a volume of 110 microlitres. The volume of a sample is approximately 10 nl and the concentration of the mixture is about 0.1 million per ml. After the first sample 205 is dispensed, the processing circuitry 155 determines that the sample in the well 105 contains no cell. Consequently, the dispenser and the well 105 are moved relative to each other such that a subsequent sample 210 will be dispensed in a different part of the well 105. When the second sample 210 is dispensed, the processing circuitry 155 again processes an image of the well 105 and determines that the well 105 contains exactly one cell 215. Accordingly, additional growth medium 160 can be provided to partly fill the well 105. Additionally, the image of the well 110 containing a single cell is output. For example, the image can be output to a storage medium 180 or can be printed on a printer. The microtiter well plate 110 is also moved such that further samples will be dispensed into a different well. Alternatively, if the current well 105 is the last well in the microtiter well plate 110 then the process stops.

Figure 3:
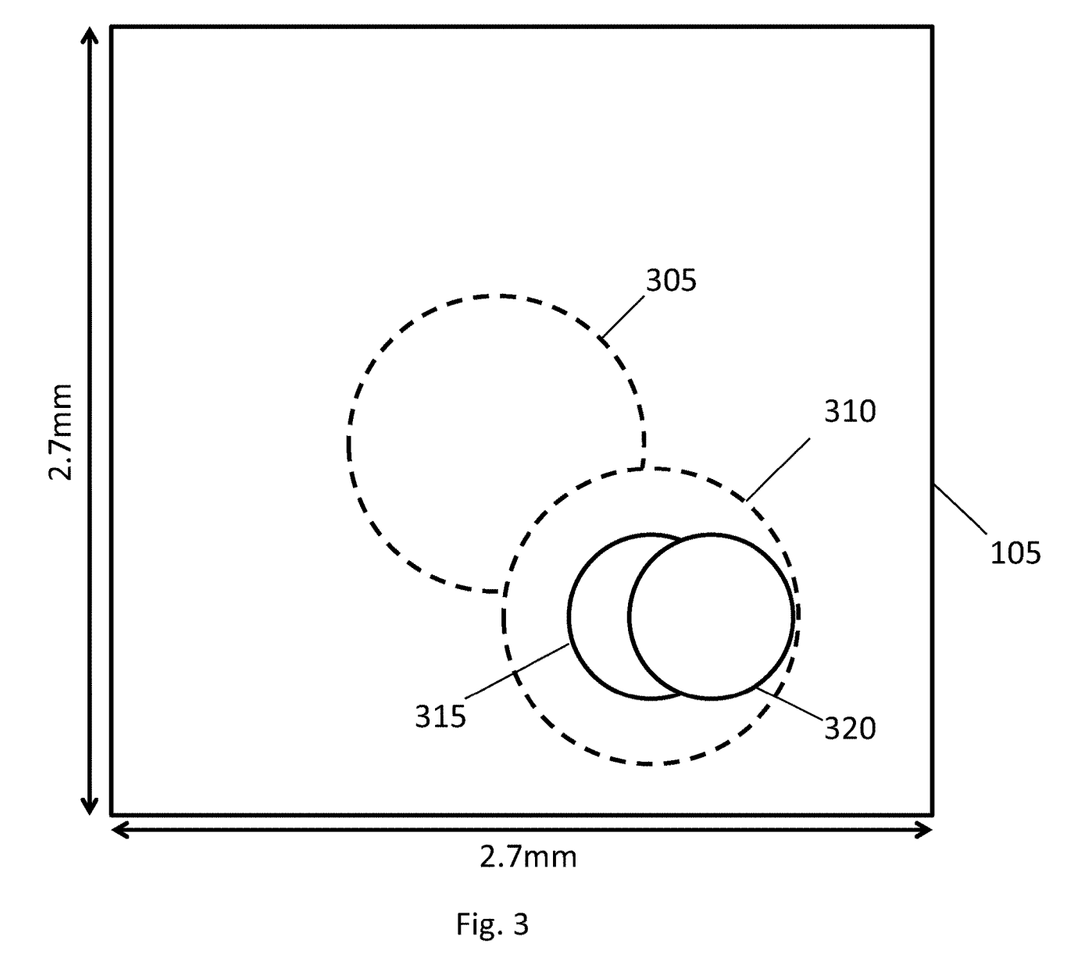
FIG. 3 shows a receptacle after dispensing a first sample having zero cells and a second sample having multiple cells.

FIG. 3 shows a receptacle, e.g. well 105 after dispensing a first sample 305 having zero cells and a second sample 310 having two cells 315, 320. In this example, again, the well 105 has an area of 2.7 mm by 2.7 mm and a volume of 110 microlitres. After the first sample 305 is dispensed, the processing circuitry 155 determines that the sample in the well 105 contains no cell. Consequently, the dispenser and the well 105 are moved relative to each other such that a subsequent sample 310 will be dispensed in a different part of the well 105. In this example, the two samples overlap slightly. When the second sample 310 is dispensed, the processing circuitry 155 again processes an image of the well 105 and determines that the well 105 now contains more than one cell (e.g. two cells 315, 320). Although the two cells 315, 320 slightly overlap each other, the processing circuitry 155 determines that there is not only one cell in the well 105. The well 105 is marked. For example, the processing circuitry 105 can immediately inform the user or alternatively can keep track of an ID number of the particular well and inform the user at the end of the process that the well should be disregarded due to having more than one cell. In any event, unless this is the final well in the microtiter well plate 110, the microtiter well plate is moved such that subsequent samples are dispensed into a different well.

Figure 4:
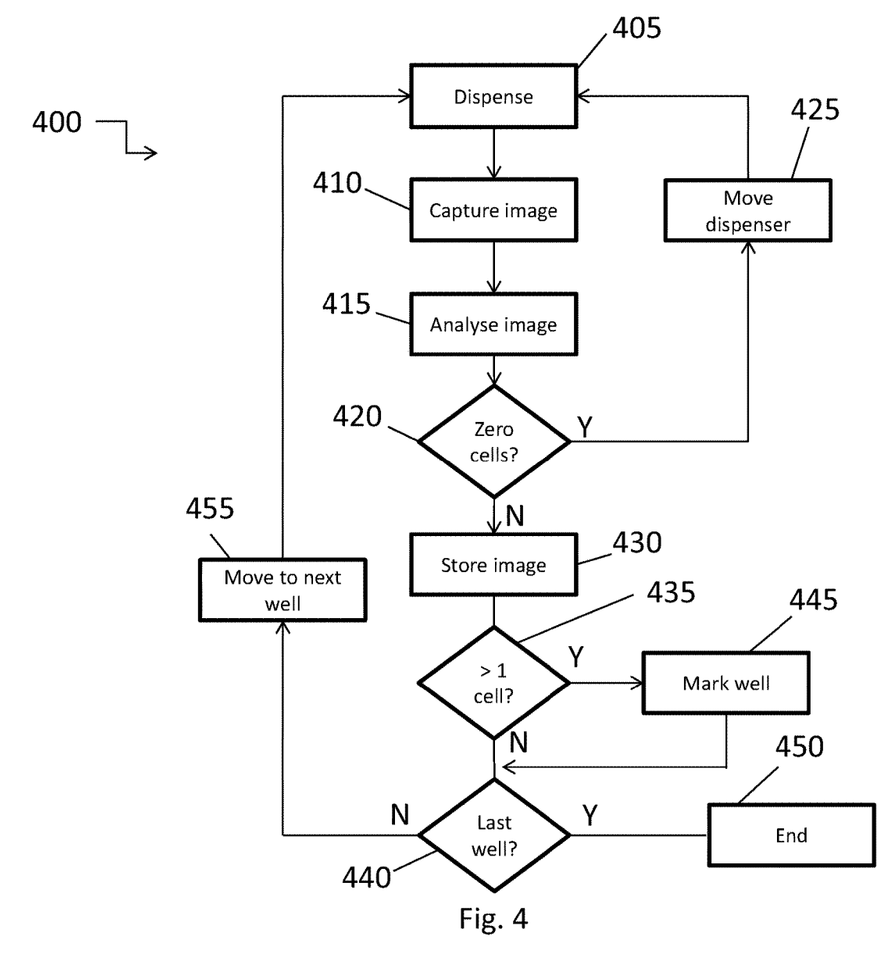
FIG. 4 shows a flowchart illustrating a method of dispensing in accordance with one embodiment.

FIG. 4 illustrates a flow chart 400 that shows a method of dispensing. In a step 405, a sample is dispensed into the current well 105. In a step 410, an image of the sample in the well 105 is captured. In a step 415, the image is analysed. It is then determined, at a step 420, whether or not the image contains zero cells. If so, then at step 425, the dispenser and the current well 105 are moved relative to each other such that a subsequent sample is dispensed into a different portion of the same well 105. Otherwise, at step 430, the image is stored for later retrieval by a user and the process proceeds to step 435. At step 435, it is determined whether or not the image contains more than one cell. If not, then the process proceeds to step 440. Otherwise, at step 445, the current well 105 is marked before the process proceeds to step 440. At step 440, it is determined whether or not the current well 105 is the last well in the microtiter well plate 110. If so, then at step 450, the process ends. Otherwise, at step 455, the microtiter well plate 110 is moved so that subsequent samples are dispensed into a different well. The process then returns to step 405 where a sample is dispensed.

Figure 5:
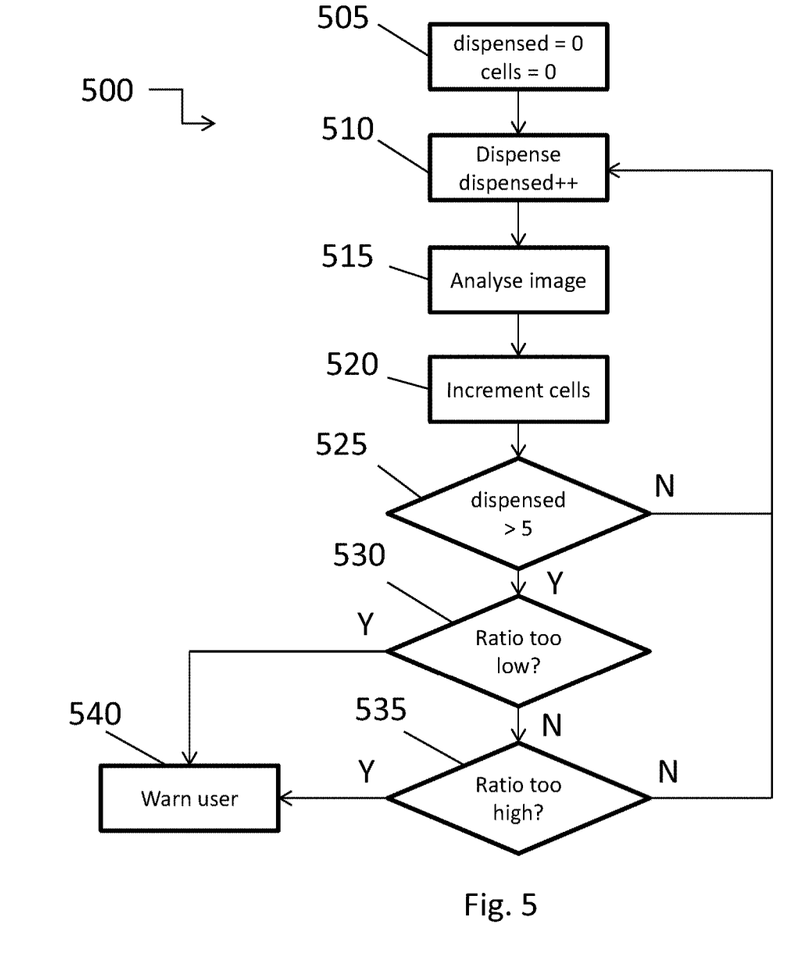
FIG. 5 shows a flowchart illustrating a method of dispensing in which a user is warned in the event that the concentration of the mixture appears to be incorrect.

It is possible to keep track of the results of the image analysis over a period of time. Using this information, it is possible to make particular inferences regarding the mixture from which samples are being taken. FIG. 5 illustrates a flowchart 500 in which such information is used. The flowchart 500 shows the process that occurs in parallel with the flowchart 400 shown in FIG. 4. Some of the steps, are common between the two flowcharts, as discussed below.

At step 505, two counters (dispensed and cells) are initialised to zero. The counter 'dispensed' counts the number of samples that are dispensed and the counter 'cells' counts the number of cells that are detected. At step 510, a sample is dispensed as previously shown with reference to step 405 in the flowchart 400 shown in FIG. 4. Additionally, the counter dispensed is incremented. At step 515, the image is analysed as per step 415 in the flowchart 400 of FIG. 4. At step 520, the counter 'cells' is incremented according to the number of cells detected within the current well 110. At step 525, it is determined whether the number of samples that have been dispensed is greater than 5. If not, the process returns to step 510. This step helps to ensure that the results are given a chance to average out before any inferences are made. At step 530, it is determined whether or not the ratio dispensed/cells is below a predetermined threshold, e.g. 0.2. In an ideal case, each well will have a single cell placed within it. However, the disadvantage of having multiple cells in a single well is significantly worse than having zero cells in a well because in the former case, the well must be marked and disregarded whereas in the latter case, further samples can be inserted. Accordingly, even though it would be desirable to always have exactly one cell per sample, the concentration of the mixture is generally chosen so that, on average, there is substantially fewer than 1 cell per sample. For example, there might only be a 37% chance of a sample containing a cell. Accordingly, the predetermined threshold may be very low. The exact selection of the threshold could be settable by a user and will, in any event, be chosen having regard to the tradeoff of desired sensitivity to the concentration being used versus the risk of a false positive of incorrectly informing the user that the concentration seems to be incorrect. In any event, if the ratio is below the threshold then at step 540, the user is warned. If not, then at step 535, it is determined whether or not the ratio dispensed/cells is above a predetermined threshold, e.g. 1.1. If so, then at step 540, the user is warned. Otherwise the process returns to step 510.

Of course, there are other ways that the system could infer that the concentration of the mixture is incorrect. For example, in another embodiment, the system could simply count the number of times that more than one cell is detected in a well. If this number were to exceed a threshold, or if a ratio of the number of times that more than one cell is detected in a well divided by the number of dispensed samples were to exceed a threshold, then the user could be warned. A second example could be to perform the steps outlined in FIGS. 4 and 5 but to arrange that all the samples are dispensed in the same receptacle, by omitting step 455 and moving to a new position in the same receptacle. In this manner, a large number of dispenses can be made and analysed in a single receptacle, purely for the purposes of determining the concentration of cells in the reservoir. This approach has the advantage that only a small number of receptacles, in this case one, is required to determine whether the correct concentration of cells is present in the reservoir. Further, if it is determined that the concentration of cells present in the reservoir is incorrect, it may be possible to repeat the process but adjusting the volume of sample dispensed in order to attempt to correctly dispense a single cell at a time. At that time, single samples can be dispensed into the remaining receptacles (if the target rate is achieved) or the user can be alerted (if the target rate cannot be achieved). The volume can be adjusted either by running the pump 135 for longer or by dispensing more than one drop of the mixture for each sample.

In the present application, the words "configured to . . . " are used to mean that an element of an apparatus has a configuration able to carry out the defined operation. In this context, a "configuration" means an arrangement or manner of interconnection of hardware or software. For example, the apparatus may have dedicated hardware which provides the defined operation, or a processor or other processing device may be programmed to perform the function. "Configured to" does not imply that the apparatus element needs to be changed in any way in order to provide the defined operation.

Although illustrative embodiments of the invention have been described in detail herein with reference to the accompanying drawings, it is to be understood that the invention is not limited to those precise embodiments, and that various changes, additions and modifications can be effected therein by one skilled in the art without departing from the scope and spirit of the invention as defined by the appended claims. For example, various combinations of the features of the dependent claims could be made with the features of the independent claims without departing from the scope of the present invention.

The invention claimed is:

1. An apparatus comprising:
a receptacle configured to receive a sample, wherein the receptacle comprises a first side comprising an opening, a second side comprising a bottom and opposite the first side, and a wall disposed between the opening and the bottom;
a sample dispenser configured to dispense the sample into the receptacle through the opening, wherein the sample dispenser is disposed proximate to the first side of the receptacle;
an image capture device configured to capture an image of the sample in the receptacle through the bottom of the receptacle, wherein the image capture device is disposed proximate to the second side of the receptacle, opposite of the receptacle from the sample dispenser; and
processing circuitry in communication with the sample dispenser and the image capture device, wherein the processing circuitry is configured to:
process the image to determine whether the receptacle contains zero cells, exactly one cell, or more than one cell, and
in response to a determination that the receptacle contains zero cells, cause the sample dispenser to dispense a further sample into the receptacle.

2. An apparatus according to claim 1, further comprising:
an actuator configured to move the sample dispenser relative to the receptacle, wherein
in response to the determination that the receptacle contains zero cells, the actuator is further configured to move the receptacle relative to the sample dispenser to dispense a further sample into the receptacle.

3. An apparatus according to claim 1, wherein
the processing circuitry is further configured such that, in response to the processing circuitry determining that the receptacle contains more than one cell, the processing circuitry performs an error action.

4. An apparatus according to claim 3, wherein
the error action comprises notifying a user that the receptacle comprises more than one cell.

5. An apparatus according to claim 3, wherein
the error action comprises storing data to indicate that the receptacle comprises more than one cell.

6. An apparatus according to claim 1, further comprising:
a growth medium dispenser to dispense growth medium into the receptacle, wherein in response to the processing circuitry determining that the receptacle contains exactly one cell, the processing circuitry is further configured to cause the growth medium dispenser to dispense growth medium into the receptacle.

7. An apparatus according to claim 1, further comprising:
an actuator to move a plurality of receptacles, including the receptacle, relative to the sample dispenser,
wherein, in response to the processing circuitry determining that the receptacle contains one or more cells, the processing circuitry is further configured to cause relative movement between the sample dispenser and the plurality of receptacles so that the sample dispenser dispenses subsequent samples into a different receptacle in the plurality of receptacles.

8. An apparatus according to claim 7, wherein,
in response to the processing circuitry determining that a first predefined proportion of dispensed samples each contain zero cells, the processing circuitry is further configured to cause a user to be alerted.

9. An apparatus according to claim 7, wherein,
in response to the processing circuitry determining that a first predefined proportion of dispensed samples each contain zero cells, the volume of each dispensed sample is increased.

10. An apparatus according to claim 8, wherein
a plurality of initially dispensed samples including the first predefined proportion of dispensed samples is dispensed into a subset of the plurality of receptacles, wherein the subset of the plurality of receptacles is less than the first predefined proportion of dispensed samples.

11. An apparatus according to claim 1, wherein,
in response to the processing circuitry determining that a second predefined proportion of dispensed samples each contain more than one cell, the processing circuitry is configured to cause a user to be alerted.

12. An apparatus according to claim 1, wherein,
in response to the processing circuitry determining that a second predefined proportion of dispensed samples each contain more than one cell, the volume of each dispensed sample is decreased.

13. An apparatus according to claim 11, wherein
a plurality of initially dispensed samples including the second predefined proportion of dispensed samples is dispensed into a subset of the plurality of receptacles, wherein the subset of the plurality of receptacles is less than the second predefined proportion of dispensed samples.

14. An apparatus according to claim 1, further comprising:
output circuitry to output the image.

15. An apparatus according to claim 1, further comprising:
a reservoir to hold a plurality of samples, connected to the sample dispenser; and
an agitator to agitate the plurality of samples in the reservoir such that cells within the plurality of samples are distributed.

16. A method comprising:
dispensing, by a sample dispenser, a sample into a receptacle through an opening, wherein the receptacle comprises a first side comprising the opening, a second side comprising a bottom and opposite the first side, and a wall disposed between the opening and the bottom, and wherein the sample dispenser is disposed proximate to the first side of the receptacle;

capturing an image of the sample in the receptacle through the bottom of the receptacle, wherein the image capture device is disposed proximate to the second side of the receptacle, opposite of the receptacle from the sample dispenser; and processing the image to determine whether the receptacle contains zero cells, exactly one cell, or more than one cell, wherein in response to determining that the receptacle contains zero cells, a further sample is dispensed into the receptacle.

* * * * *

UNITED STATES PATENT AND TRADEMARK OFFICE
CERTIFICATE OF CORRECTION

PATENT NO. : 11,279,910 B2
APPLICATION NO. : 15/603184
DATED : March 22, 2022
INVENTOR(S) : Figg et al.

It is certified that error appears in the above-identified patent and that said Letters Patent is hereby corrected as shown below:

In the Claims

At Column 10, Claim 6, Line 6, the words "wherein in response to the …" should read -- wherein, in response to the --.

Signed and Sealed this
Fifth Day of September, 2023

Katherine Kelly Vidal
*Director of the United States Patent and Trademark Office*